United States Patent [19]

Gnuechtel et al.

[11] Patent Number: 5,036,706
[45] Date of Patent: Aug. 6, 1991

[54] SONIC WEB BREAK DETECTOR

[75] Inventors: Herman C. Gnuechtel, Arlington Heights; Harvey A. Brodsky, Evanston, both of Ill.

[73] Assignee: Web Printing Controls Co., Inc., Lake Barrington, Ill.

[21] Appl. No.: 390,783

[22] Filed: Aug. 8, 1989

[51] Int. Cl.⁵ .................... G01N 9/24; G08B 21/00
[52] U.S. Cl. .................................... 73/597; 340/675
[58] Field of Search .............. 73/597, 598, 627, 628, 73/620, 159; 340/675, 674; 367/93, 95, 97

[56] References Cited

U.S. PATENT DOCUMENTS

| | | | |
|---|---|---|---|
| 3,431,549 | 3/1969 | De Tullio et al. | 367/93 |
| 3,675,190 | 7/1972 | Auer, Jr. et al. | 367/93 |
| 3,922,629 | 11/1975 | Hayakawa | 367/93 |
| 3,928,844 | 12/1975 | Meihofer | 340/259 |
| 3,987,665 | 10/1976 | Hansen | 73/159 |
| 4,131,872 | 12/1978 | Inoue et al. | 367/93 |
| 4,221,329 | 9/1980 | Schneider | 235/458 |
| 4,335,603 | 6/1982 | Locke | 73/159 |
| 4,493,065 | 1/1985 | Sword, Jr. | 367/96 |
| 4,513,404 | 4/1985 | Huggins | 340/674 |
| 4,519,249 | 5/1985 | Hunt | 73/596 |

Primary Examiner—Hezron E. Williams
Assistant Examiner—Louis M. Arana
Attorney, Agent, or Firm—Welsh & Katz

[57] ABSTRACT

A web break detector which utilizes sonic signals to detect the occurrence of a break in a moving web in web handling machinery. A separate sonic transmitter and receiver transducer are utilized to provide improved speed of detection, and enhanced reliability. The dual transducer detector can also be placed closer to the web to enhance reliability and efficiency. Multiplexing is utilized to permit multiple detectors to be operated with reduced complexity and minimal mutual interference. The transmitting transducer is triggered to emit a sonic burst for a predetermined time period and at a predetermined rate. The receiving transducer is activated for a predetermined time duration beginning a predetermined delay period after the sonic burst is triggered and generates a detection signal in response to receiving the reflected burst. The absence of the detection signal causes generation of a control signal to stop the web handling machinery.

34 Claims, 5 Drawing Sheets

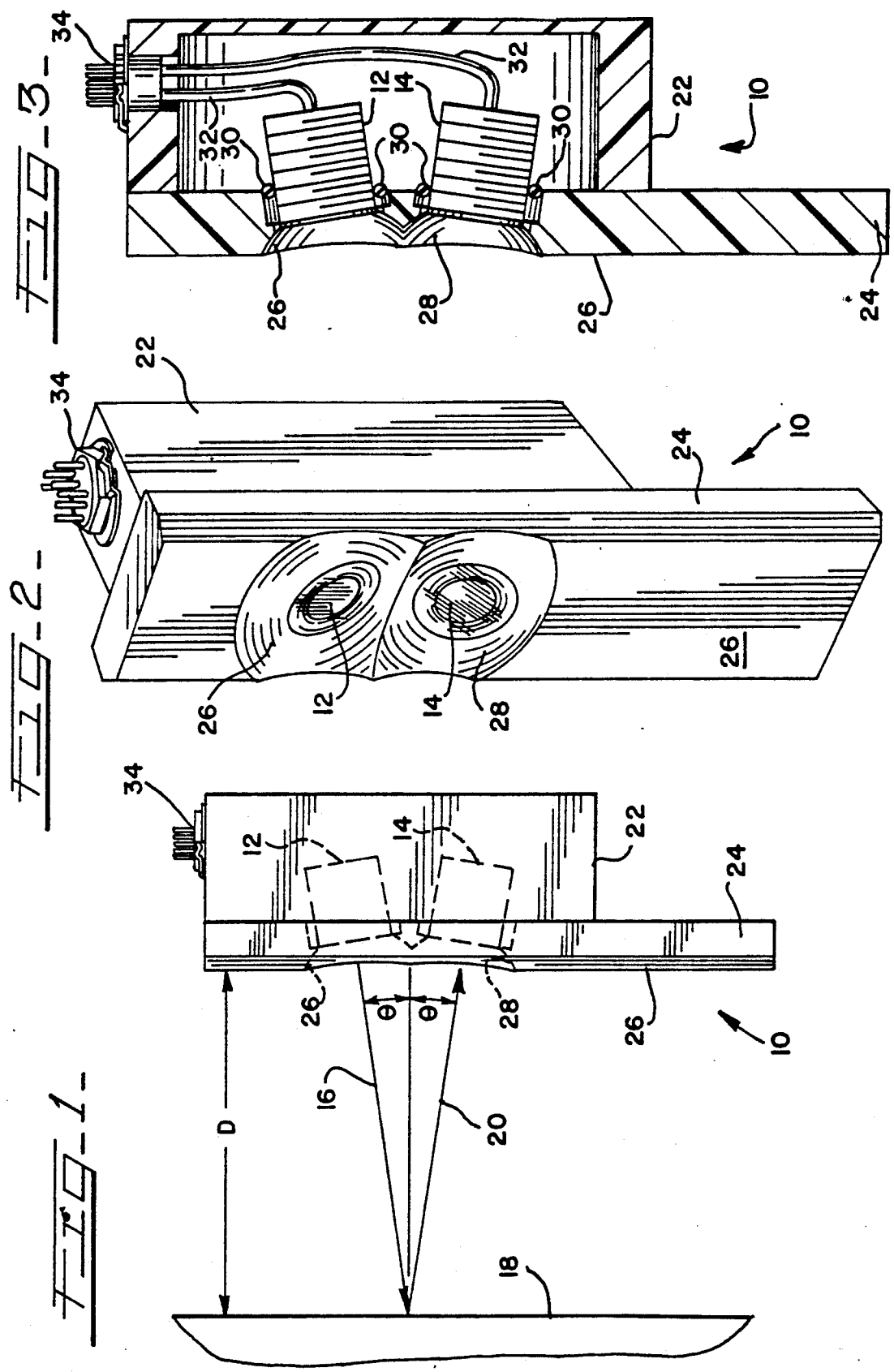

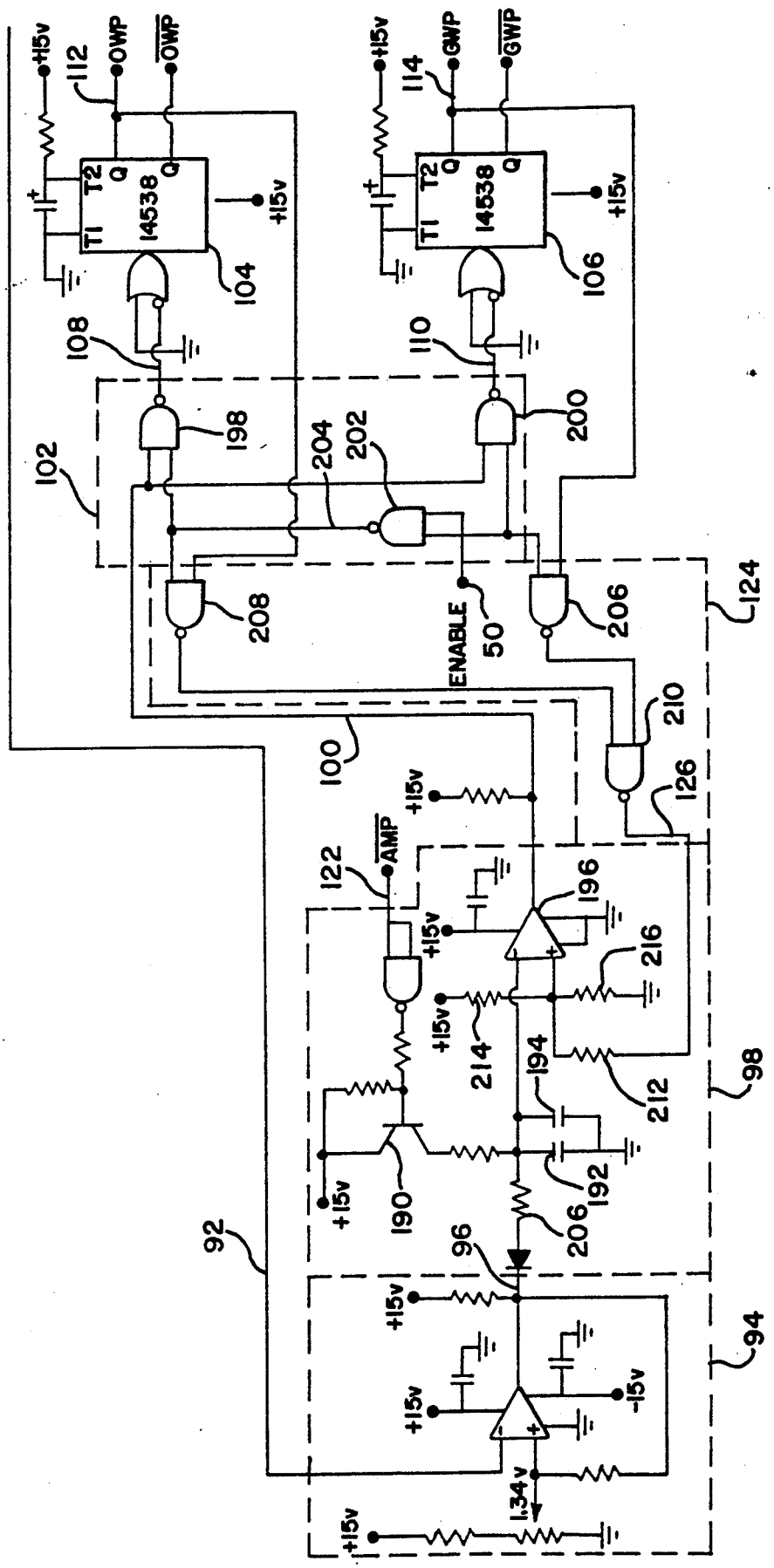

SONIC WEB BREAK DETECTOR

The present invention generally relates to an improved web monitoring and control apparatus for use with web handling machinery such as printing presses or the like which handle a generally continuously moving web. The present invention more particularly relates to a web break detector of the type which utilizes sonics as opposed to visible or invisible light radiation.

Many industries utilize machinery for handling generally continuous webs of material, including, but certainly not limited to fabrics, plastic films, metal foil, paper and the like. While some of these materials are inherently quite strong and therefore are not particularly susceptible to breakage, others are. High speed printing presses which print on various grades of paper are certainly susceptible of breakage while moving through the press, and when breakage occurs, it is necessary, if not essential, to quickly detect such a breakage and shut down the press. Otherwise the paper may wrap on printing rolls and create a build up that will damage the press. Additionally, from an operational standpoint, a printing company experiences a significant cost whenever a press has to be shut down during a printing run and if the problem can be quickly corrected, the costs can at least be minimized.

It is for these reasons that web monitoring systems have been utilizes to detect the occurrence of a web break and these detectors have utilized many different kinds of monitoring devices, including photoelectric circuits, systems which utilize infrared energy, including those which direct a beam of light to the web, and detect the reflected light with an infrared detector. Obviously, if a web break has occurred, there will be no reflected light and such condition is detected and the press is automatically shut down through appropriate interconnections and controls. While such infrared and photoelectric type of systems often function quite well, they do have their attendant disadvantages which primarily reside in the fact that ink, dust and the like, which are often present in the environment of a printing press, tend to contaminate the lenses of such detection units which attenuates the signal level detected and increases the likelihood of a false web break indication during operation.

More recently there has been more emphasis placed on the development of web break detectors that utilize sonic transmitters and receivers, rather than visible or invisible light circuits. Such sonic detectors are less sensitive to signal attenuation caused by dust, ink or the like. Some of the systems utilize the sonic detector that is available from Polaroid which is used in its SX70 camera, among other cameras, and these detectors have a screenlike grid over the unit which is sufficiently open that dust and ink can penetrate it and detrimentally affect its operation. One way in which such units are cleaned is to use a spray cleaner which penetrates through the grid to the inner surface, but that type of cleaning will not effectively clean a glob of ink that may be present. In that situation, it is often necessary to replace the sonic detector/transmitter transducer in the unit.

With the above in mind, it is a primary object of the present invention to provide an improved web monitoring and control apparatus of the type which utilizes sonics, which apparatus has many desirable attributes when used in conjunction with web handling machinery.

Another object of the present invention is to provide such an improved sonic web break detector which has superior operating characteristics, is reliable in its operation and which can be easily cleaned when dirt, dust and/or ink is present on the critical surfaces.

Yet another object of the present invention is to provide such an improved sonic web break detector which is capable of operating from a very short distance relative to the web, i.e., approximately three inches or less, which makes the unit physically compatible with prior infrared detectors and therefore can be easily retrofitted on existing press installations by mere substitution of a relatively few physical modules.

Still another object of the present invention is to provide such an improved sonic web break detector which utilizes a sonic transmitter transducer that is separate and functionally independent of the sonic receiver transducer, which results in greater speed in detection of a web break and also enhances efficient and reliable operation.

Another object of the present invention is to provide such an improved sonic web detector that can be placed close to the web, thereby enhancing its operating efficiency and reliability, due to the fact that the distance in which sound refraction can occur is reduced.

Still another object of the present invention lies in the provision of providing multiplexing of certain signals within the electrical circuitry of the present invention so that a pair of web break detector modules located on the gear and operator sides of the edges of the web are monitored, with the multiplexing reducing the complexity of the circuitry and effectively virtually eliminating interference that may otherwise occur as a result of both of the pair of units operating at the same time.

Other objects and advantages will become apparent upon reading the following detailed description, while referring to the attached drawings, in which:

FIG. 1 is an elevation of a portion of the apparatus of the present invention shown in connection with a portion of a generally continuous web of material;

FIG. 2 is a perspective view of a portion of the apparatus of the present invention, and showing the module containing the sonic transmitter and receiver units;

FIG. 3 is a cross section of the portion of the apparatus shown in FIG. 2, taken generally along the line 3—3 thereof;

FIGS. 5A, 5B and 5C, taken together, comprise an electrical schematic circuit diagram of the present invention and illustrating the detailed circuitry shown in the block diagram of FIG. 4.

DETAILED DESCRIPTION

Figure 4:
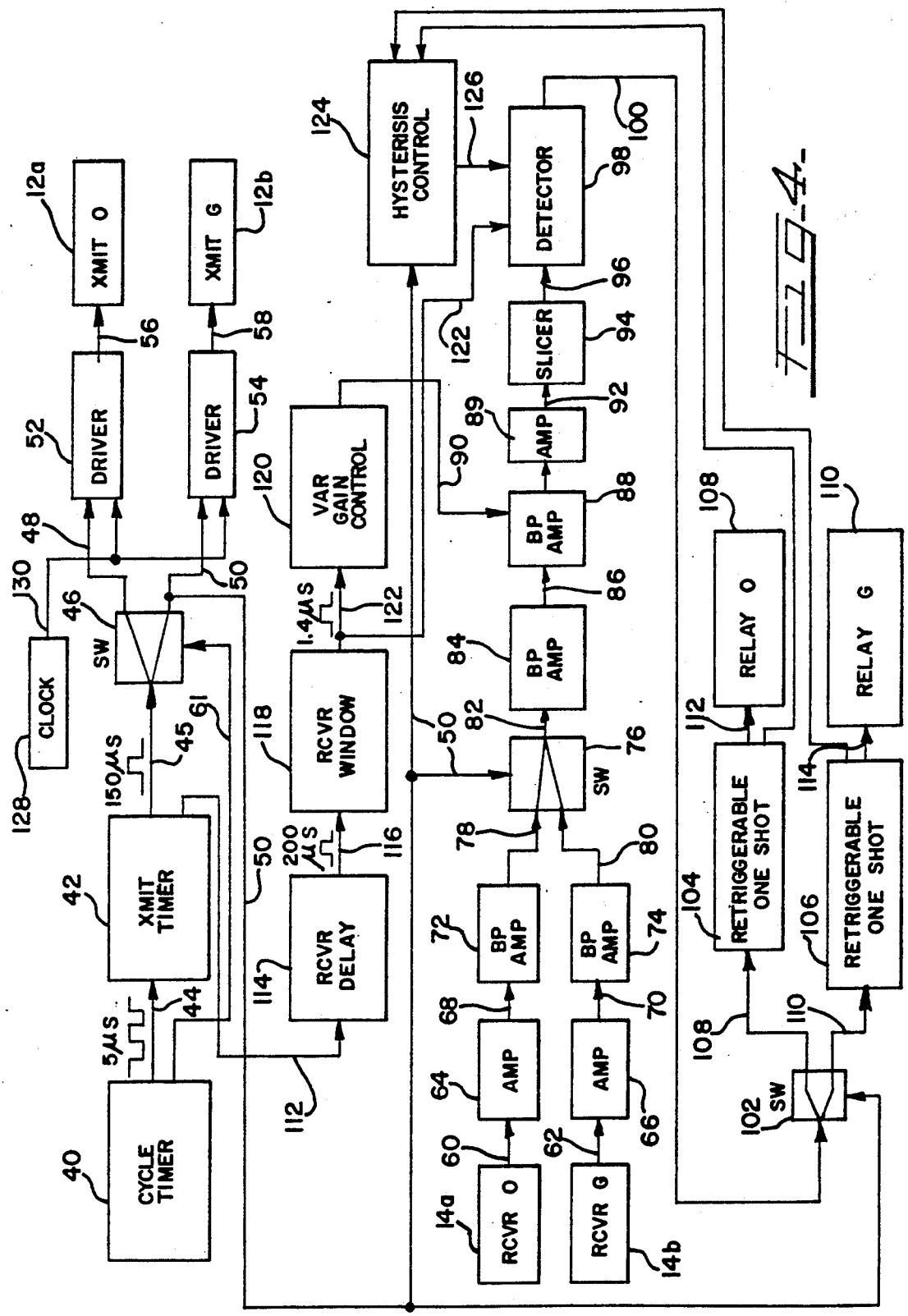
FIG. 4 is a schematic block diagram of the apparatus of the present invention.

Broadly stated, the present invention comprises an apparatus for monitoring a continuously moving web of material, such as fabric, metal, plastic, paper and/or the like, and particularly relates to such an apparatus which will monitor the presence of a paper web within a web printing press. Such apparatus is generally known in the trade as a web break detector. Web break detectors are interconnected with the printing presses onto which they are installed as accessories for controlling the press to shut the press down if the paper being printed breaks. Such paper breaks generally occur at one of the outside edges of the press and for this reason web break detector modules are usually located at least on the outside edge portion and sometimes interiorly if more than two detector modules are installed. It is well known that if paper breaks and begins wrapping the print rolls of a printing press, they can increase the diameter to such an extent that they begin to interfere with other cooperating rolls and create such tremendous pressures that they can quickly cause substantial damage to the press. Therefore, it is highly desirable if not necessary to quickly shut down the press in the event of a paper breakage. Since printing presses that print a continuous web of paper now are tremendously expensive and may exceed $5 million, it is highly desirable to keep such a presses operating without significant down time. It is estimated that a printing company looses approximately $350.00 or more every time the printing press is shut down. Obviously, if the press is damaged so that it is shut down for an extended time necessary to make repairs, the loss that may be experienced may be substantially higher. It is for these reasons that effective web break detector systems are highly desirable accessories that are installed on virtually all modern web printing presses. It is also for these reasons that it is highly desirable, if not necessary, that such web break detectors operate efficiently and effectively. Not only is it essential that they detect an actual web break and shut the press down in response to such detection, but it is also extremely important that the apparatus not trigger such a shutdown falsely. It is well known that the environment of a printing press is one which is not particularly clean in that there is a significant amount of dust generated from the moving web of paper, and also ink particles, and occasionally globs of ink, are typically cast into the air and can light on virtually any surface, particularly the web break detector surfaces. A well known type of web break detector utilizes either visible or invisible, i.e., infrared, light energy to define light circuits which are directed to the web, bounce off the web and are detected by a light sensor. Such light circuit type of web break detectors are particularly susceptible to being contaminated by dust and/or ink and have to be frequently cleaned.

The present invention relates to a sonic type of web break detector which utilizes short bursts of high frequency sound energy (which may be referred to herein as a "chirp") which is directed toward the web, reflects from the web and is then detected by a sonic detector. Each sonic web break detector module includes a sonic transmitting piezoelectric transducer which produces the chirp that is separate and independent of a sonic receiver or detector which detects the pressure of a reflected chirp. Associated circuitry controls the operation of the transmitter and receiver such that only one of a pair of detector units operates at any one time and through use of multiplexing techniques, certain portions of the circuitry are effectively utilized with respect to the operation of both ones of a pair of modules, thereby reducing manufacturing costs. The apparatus of the present invention is also desirable in the sense that it can be placed very close to the moving web which increases its reliability and also facilitates retrofitting into mounting structures that may have been originally installed for an infrared type of system as manufactured by Web Printing Controls Co., Inc. of Barrington, Ill., the assignee of the present invention. In addition to the facility of easily retrofitting such sonic detector modules, the placement of the detector modules more closely to the web, i.e., on the order of approximately three inches therefrom, the detector modules more reliably detect the reflected sonic signal or chirp than would otherwise occur if the unit were located farther from the web. This is due in part to the phenomenon of the sound being refracted as it moves through the air, such refraction being caused by temperature variation and also by the speed of movement of the moving web during a printing operation. It has been found that temperature variations tend to change the direction of the reflected sound signal as does the rapid movement of the web. By minimizing the distance from the detector unit to the web, such refraction is minimized, which results in the chirp striking the receiver where it is designed to strike, which concomitantly results in a stronger electrical signal being generated by the receiver transducer.

Another desirable feature of the present web break detector apparatus lies in the provision of utilizing a significantly higher frequency sound burst or chirp during operation than typical piezoelectric transducers utilize, i.e., the present invention utilizing a 215 kHz burst or chirp whereas conventional piezoelectric transducers typically operate at approximately 50 kHz. The use of the higher frequency signal minimizes the false detection of a reflected chirp, because extraneous 50 kHz sound energy often exists in pressrooms, whereas 215 kHz energy typically does not. The present invention also creates a window for operating the receiver transducer, which window is set to open when the reflected chirp should be received and closed when it is expected to have expired. Also, because the sensitivity of receiver piezoelectric transducers can be detrimentally affected by dirt, dust, ink and the like, the receiving surface of the piezoelectric transducer must be cleaned. Because some conventional transducers often have a screenlike grid over their front surface, it is often difficult to effectively clean them. The present invention utilizes a thin film adhesively attached to the transducers that facilitates easy cleaning while not appreciably degrading the sensitivity of the transducer.

Turning now to the drawings, and particularly FIGS. 1–3, a sonic web break detector module, indicated generally at 10, is illustrated and includes the piezoelectric transducer used as a transmitter 12 and another piezoelectric transducer used as a receiver at 14. The transmitters transmits a sonic signal or chirp schematically illustrated along the line 16 which strikes the web 18, is reflected along the line 20 to the receiver 14. The distance D between the transducers 12 and 14 and the web 18 is preferably within the range of about 1½ inches to about 6 inches and preferably approximately 3 inches. The angle θ is relatively narrow, within the range of approximately 5 to 10 and preferably about 7. As with the infrared type of detector, it is preferred that the angle θ be relatively small so that flutter of the web, i.e., movement of the web toward and away from the transducers, does not appreciably affect the operation of the apparatus.

Turning now to FIG. 2, which illustrates a perspective view of a sonic web break detector module such as that shown in FIG. 1, it includes a generally rectangular housing 22 with an elongated face member 24 both of which are attached to one another and contain the transmitter 12 and receiver 14 therewithin. The module has a face member 24 having a front surface 26 with generally circular, concave in cross-section depressions 28 and 30 located adjacent the transmitter and receiver respectively, which provide the dual function of acting as a sound dish for receiving the reflected chirp and also recess the transmitter and receiver from the surface 26 thereof to provide an added degree of isolation and therefore protection for the transmitter and receiver. Additionally, the concave depressions facilitate easy cleaning, and provide an aesthetically pleasing appearance for the module. In this regard, a design patent application, assigned to the same assignee as the present application, has been concurrently filed. The configuration of these relationships is also illustrated in the cross sectional view of FIG. 3. The sonic transmitter 12 and receiver 14 are piezoelectric transducers which are physically the same identical units, but merely operating in differing modes. The units can be, for example, model E-201A-215 transducers, as manufactured by the Masa Corporation of Hingham, Mass. In the present invention, the transducer units are fitted within the front member 24 with an epoxy adhesive 30 in such a way that there is no rigid metal-to-metal contact between the cylindrical portion, and the front member 24. While the term "metal-to-metal" has been used, it is not meant literally. It is preferred that the container 22 and face member 24 be fabricated from aluminum or other metal, but a plastic material may also be used. Because of the high amplification of the signals that are received by receiver transducer 14, it is important that the epoxy be used to hold the units 12 and 24 in the face member 24 in such a way that no rigid contact other than with the epoxy is made with the face member 24 to reduce the coupling of the receiver from the transmitter. It has been found that with the high amounts of amplification that will be hereinafter described, if there is any physical coupling in addition to the epoxy, the operation of the unit is severely detrimentally affected. Each of the units 12 and 14 has an electrical lead 32 which stems from the units to a connector 34 to which another suitable connector (not shown) interconnects with a circuit board in a control unit that is located nearby on or adjacent the printing press to which the units are supplied. As previously mentioned, it is preferred that at least two of the modules 10 be provided and located on opposite sides of the web to detect tears or breaks in the web which usually occur at the outer edges thereof. A printing press may have a number of pairs of such units located at various positions on the press as is conventional.

The epoxy 30 is preferably designated SR-9 as manufactured by Adhesive Research Corporation of Glen Rock, Pa., but may be another adhesive, which does not appreciably degrade over time or under relatively high temperature conditions, is sufficiently resilient that it provides a sound dampening function for the reasons described. The thickness of the preferred adhesive is approximately 1 mil.

Because the environment in which the units 10 are placed, it is desirable to be able to clean the transmitter and receiver 12 and 14 so that the desired signal levels can be maintained. To this end, the units 12 and 14 have a thin layer 38 of film applied to the outer surface of the transducer units which provides a protective surface through which sound can pass, but provides protection against having dirt, ink or the like penetrate to the interior of the transducer units. It is preferred that the thin film be impervious to solvents that are typically utilized in printing press areas, that it accept an adhesive layer, that it be of a thickness of approximately 0.5–4 mils, and preferably 1 mil. It has been found that a 0.5 mil film is not sufficiently strong and that a 5 mil thickness film is too thick and that it provides too much attenuation of the sound signal that is intended to pass through the film. It is preferred that the film be Kapton as manufactured by the DuPont Corporation of Wilmington, Del. It is also important the front surface of the transducer units 12 and 14 be substantially flat surfaces within approximately 5/1000 of an inch across the entire unit. This is highly desirable to maintain the film in its correct position while preventing it from shearing under normal conditions. If the outer surface is such that the outer periphery of the unit is higher than the center, then the film has a tendency to unseat which increases the attenuation of the sound signal and detrimentally affects the operation of the unit. Conversely, if the inner surface is raised relative to the periphery thereof, the interface between the outer periphery and the center surface can provide an edge which results in a shearing of the film. If such shearing occurs, it permit solvent to enter into the interior of the transducer and thereby damage the transducer.

With respect to the operation of the associated circuitry of the present invention, it is shown in the schematic block diagram of FIG. 4 and includes a cycle timer 40 which generates a square wave having a cycle duration of approximately 5 milliseconds which is fed to a transmit timer 42 via line 45 and the transmit timer 42 produces a short pulse of 150 microseconds on line 44 once during every 5 milliseconds. The line 45 is applied to a multiplexing switch 46 which has lines 48 and 50 extending to drivers 52 and 54, which are in turn connected to transmitters 12a and 12b via lines 56 and 58. As a result of the multiplexing operation, each of the drivers is alternatingly triggered, and each is triggered at a rate of 10 milliseconds. The drivers 52 and 54 are push/pull drivers which generate a 215 kHz signal having a duration of 150 microseconds as determined by the transmit timer 42. Once the signal has been generated by either of the transmitters, it is directed toward the web in the manner as previously described, strikes the web if it is present and is reflected so that it is detected by the receiver. The switch 46 is controlled by the cycle timer 40 via line 61 and line 50 from switch 46 also extends to and controls other portions of the circuitry and effectively multiplexes the pair of transmitters so that transmitter 12a which is located on the operator side of the press is operated at a time when the other transmitter on the gear side of the press 58 is operated. By multiplexing the operation of the two transmitters, there is less likelihood of interference being created by operating both of the transmitters simultaneously.

The schematic block diagram shows the receiver transducers 14a and 14b for the gear and operator sides, respectively, are connected via lines 60 and 62 to amplifier stages 64 and 66, respectively which in turn are connected via lines 68 and 70 to bandpass amplifiers 72 and 74. The outputs of these amplifiers are connected to another multiplexing switch 76 via lines 78 and 80 and the selected output is applied via line 82 to yet another bandpass amplifier 84, the output of which appears on line 86. This line is connected to yet another bandpass amplifier stage 88 that is of the type which has a variable gain control via input line 90. The amplifier stage 88 is connected to another amplifier 89 and its output is applied on line 92 to a slicer 94 which conditions the signal and outputs it to line 96 where it is connected to a detector 98 which detects the presence of the signal if the web is present. The detector output is applied on line 100 that is connected to yet another multiplexing switch 102 and it is connected to one of two retriggerable monostable multivibrators or one-shots 104 and 106 via lines 108 and 110 which confirm the presence of the detected chirp or confirm its absence and control one of the operator or gear side relays 108 and 110 via lines 112 and 114. The relays are connected to the control circuitry of the press and are operable to shut it down in the event that a break in the web has been detected.

In accordance with an important aspect of the present invention, it should be appreciated that the operator side module should be controlled to detect the reflected chirp when a web is present at the appropriate time and that the gear side detector be activated to detect the chirp transmitted by transmitter 12b after it has transmitted it. In accordance with this operation, the transmit timer 40 has an output line 112 that extends to a represents the time required for the chirp to be transmitted, reach the web, be reflected and almost reach the receiver 14. The 200 microsecond pulse is applied via line 116 to a receiver window circuit 118 which generates a pulse having a duration of 1.4 milliseconds which is applied to a variable gain control 120 via line 122 and this variable gain control circuit controls the bandpass amplifier 88 to increase the gain over time and thereby control the amplitude of the signal applied to the slicer. Such increasing of the gain is necessary for the system to operate properly. The receiver window pulse thereby activates the detector for a period of approximately 1.4 milliseconds which is positioned in time to receive the reflected chirp and detect the same. This substantially reduces the probability that spurious sound signals may be falsely detected since the circuitry is disabled except during that period of time when the 1.4 milliseconds window is open.

The line 50 from the transmit timer 40 also extends to a hysteresis control circuit 124 which has output line 126 that is applied to the detector 98. This circuitry alters the reference voltage for a comparator that detects the absence of the detected chirp, i.e., a web break, in the form of the signal from the slicer and provides a true signal on output line 100 at a particular voltage, e.g., 5 volts, but once the break has been detected, the comparing voltage is then changed to a higher level for a subsequent operation, so that there will not be any rapid on/off operation of the comparator.

If a break in the web has been detected, the retriggerable one-shot 104 will time out and provide an output that causes relay 108 to shut down the press. In this regard, the timing of the retriggerable one shot is set such that more than two successive cycles generated from the cycle timer 40 are required. More specifically, the chirps are generated at a 10 millisecond rate, and the retriggerable one shot is preferably set to time out after 25 milliseconds. Thus, the presence of a reflected chirp which is detected causes the retriggerable one-shot to be retriggered and its output will remain at the level that controls the relay so that the press continues to run.

The frequency of the sonic signal produced by the transmitters 12a and 12b is effectively determined by a clock circuit 128 which has output line 130 that is connected to each of the drivers 52 and 54 so that when the switch 46 enables one or the other of the drivers 52 and 54, and is preferably about 215 kHz. The 215 kHz signal from the clock circuit is applied to the push-pull driver 52 and thereby drives one of the transmitters 12a or 12b causing the chirp to be transmitted.

Figure 5A:
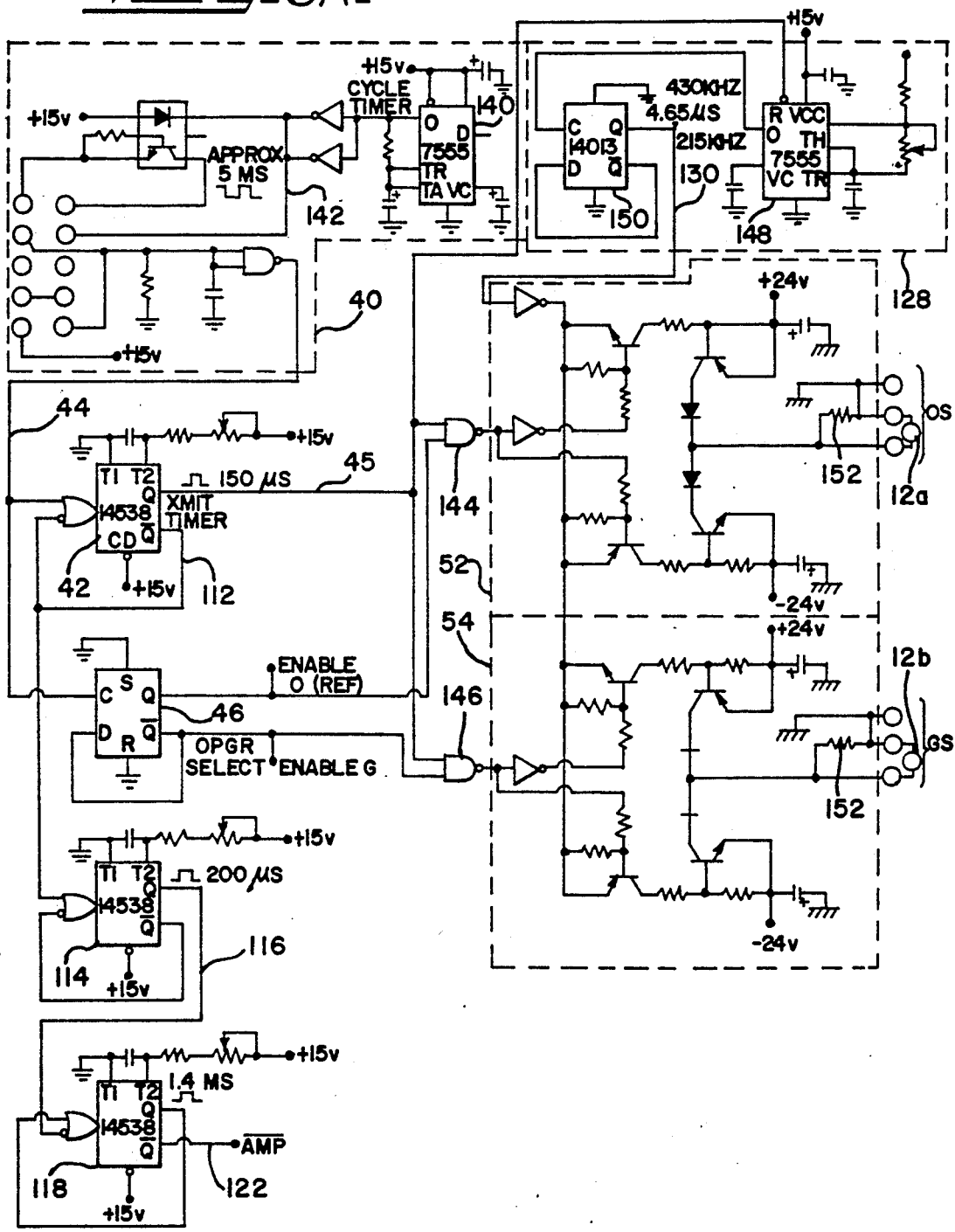
Figure 5B:
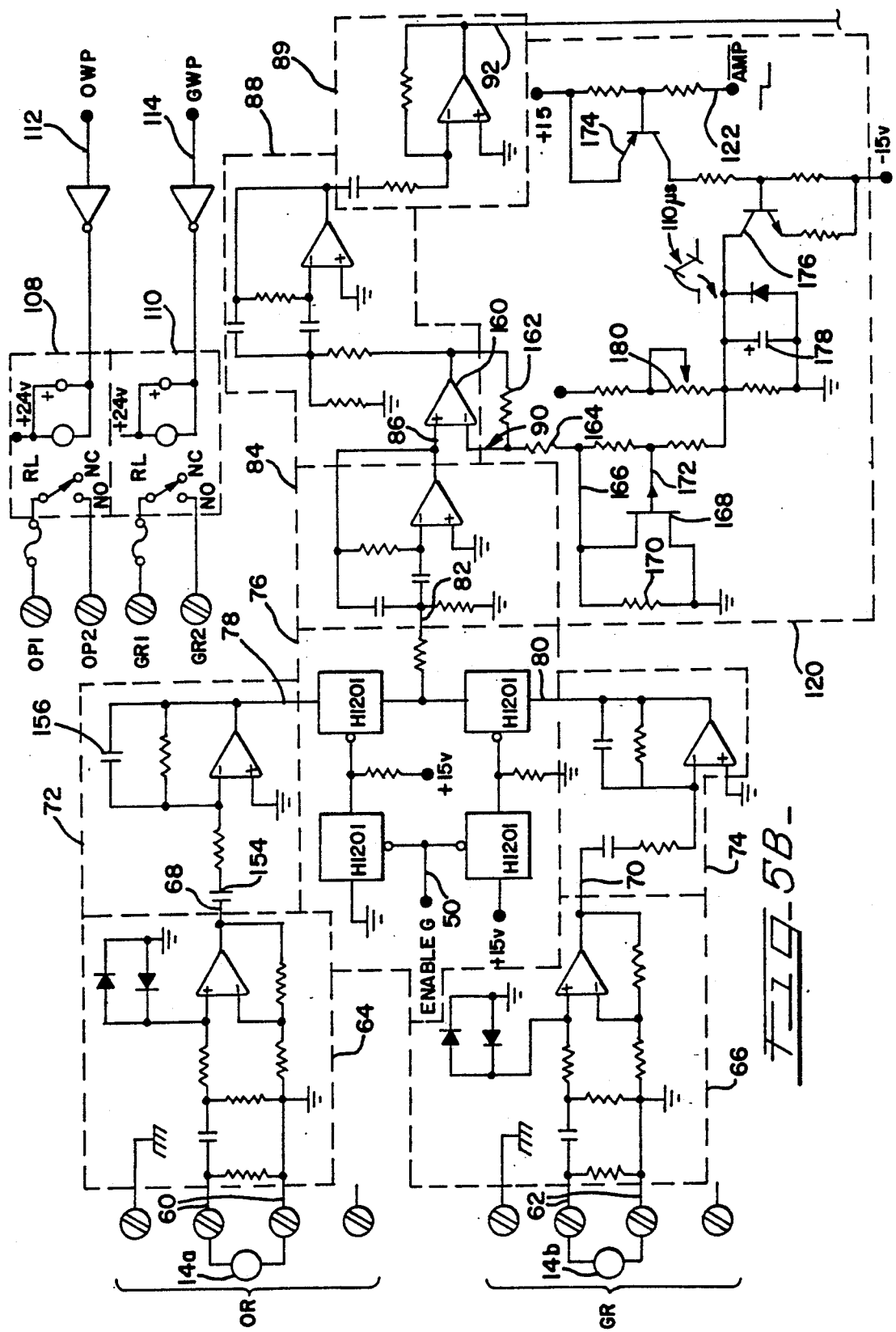

Turning to the schematic circuit diagrams shown in FIGS. 5A, 5B and 5C, it should be understood that these circuit diagrams comprise the specific circuitry that is used to carry out the operation of the schematic block diagram illustrated in FIG. 4 as has been described. Where possible, reference numbers illustrated in FIG. 4 will be applied to the circuitry shown in FIGS. 5A, 5B and 5C. With regard to the transmitting portion of the circuitry and referring to FIG. 5A, the cycle timer 40 includes a clock 140 which produces a square wave having a period of 5 milliseconds on line 142 which is gated to produce output line 140 that carries the 5 milliseconds signal to the transmit timer 42 and to the switch 46 which is a conventional flip-flop that the cycle timer clocks every 5 milliseconds. The output of the transmit timer is a 150 microseconds pulse appearing on line 45 that is applied to a NAND gate 144 as well as to another NAND gate 146 which are in turn connected to the drivers 52 and 54, respectively. The clock 128 comprises a clock 148 which is connected to a flip-flop 150 which operates as a divide-by-two divider and divides a 430 kHz output generated by the clock 148 to 215 kHz on line 130 which extends to both drivers 52 and 54. The 215 kHz signal is also a perfect duty cycle square wave which is not a characteristic of the 430 kHz signal from the clock 148. Each of the drivers 52 and 54 is identical to one another and each comprise a bi-polar push-pull driver that have a tristating capability and is operable to drive the transducer 12a or 12b by alternately applying +24 volts and −24 volts to them when the driver is turned on. The transmit timer 42 and switch 46, when gated by gates 144 and 146, are operable to turn on either the driver 52 or 54. During operation, the transmit timer provides the 150 microseconds pulse to the NAND gate 144 and 146, and depending upon the state of the switch 46, provides a true signal on one or the other of the gates 144 and 146 to turn on the appropriate driver.

A resistor 150 is provided in the circuitry of each of the drivers 52 and 54 is important in the operation of the transmitter for the reason that when a driver is turned off, the transducer then sees the resistors 150 as its load and the load causes a dampening action of the transducer which effectively turns it off. The transducer is sufficiently sensitive that if the resistor were not present, virtually any significant disturbance would start the transducer ringing which could create problems in the operation. Referring to the transmit timer 42, its $\overline{Q}$ line 152 is applied to trigger a receiver delay monostable multivibrator at the end of the 150 microseconds period via line 112 and the receiver delay one-shot is then applied via line 116 to the receiver window one-shot 118 which produces a 1.4 milliseconds signal for enabling a variable gain control 120 via line 122, which line also extends to activate the detector 98. The receiver delay 114 pulse of 200 microseconds allows the transmitter disturbances to subside and during that period, the sonic signal generated by the transducer 12a or 12b is still in transit, at the termination of the 200 microsecond pulse, the receiver window one-shot 118 is triggered and the detector is turned on for a period of 1.4 milliseconds which is the time during which a reflected signal should be present if the web is also present. Conversely, if the web has torn or is broken, then the detector will detect the absence of a chirp.

Referring to the receiver circuitry shown on FIG. 5B and 5C, the receiver transducers 14a and 14b are shown to be connected to respective amplifiers 64 and 66 by line 60 and 62. The amplifiers amplify a.c. signals that are passed from the transducers. The output of the amplifier 64 is applied to a bandpass amplifier 72 by line 68 with capacitors 154 and capacitor 156 The output of the bandpass amplifier, appears on line 78 that is connected to the switch 76 which demultiplexes the signal in accordance with the level of line 50 which thereby determines which transducer signal is to be processed through the remainder of the circuitry. The switch 76 has output line 82 that is connected to bandpass amplifier 84, which in turn is connected by line 86 to bandpass amplifier 88 that is capable of having its gain controlled by the variable gain control circuitry 120.

The amplifier 88 is controlled by the variable gain control 120 via line 90 to control the gain produced by the amplifier 88 in such a way that initially a minimal gain is produced when the receiver window is opened, but which gain increases through a portion of the duration of the 1.4 milliseconds window. This is necessary because of the ringing problem associated with such sonic transducers. In the absence of such a variable gain control, any minor tolerance problem may easily result in ringing which would be detected as a false signal.

An operational amplifier 160 has its negative input line 90 connected to resistors 162 and 164, resistor 164 of which is connected by line 166 to a field effect transistor or FET 168 and to a resistor 170. When FET 168 is controlled to provide minimum resistance, the gain of the operational amplifier 160 is approximately 13, which is preferred and is determined by the ratio of the value of resistor 162 relative to that of resistor 164. When the resistance of the FET 168 is increased to infinity, the resistor 170 is then in series with resistor 164 and the gain of the amplifier 160 is then reduced to less than one and actually functions as an attenuator. When the FET 168 has a zero resistance, it effectively short circuits the resistor 170.

The operation of the FET 168 is controlled by circuitry connected to its gate, i.e., line 172 and operates as follows. When line 122 is switched low, a transistor 174 turns on, which turns on the transistor 176, thereby linearly discharging capacitor 178, which over time turns on the FET 168 and removes the resistor 170 from the circuit. When line 122 is high or a logical one state, transistor 174 is switched off, which means the transistor 176 is off, and in that condition the capacitor 178 is charged to a level determined by the variable resistor 180 in combination with the other resistors connected thereto, so that the FET 168 is not conducting, thereby adding the resistor 170 to the circuit which reduces the gain of the amplifier 160 to essentially unity. In the illustrated embodiment, the gain of the system through the amplifier 88 may, for example, have a gain when in the high gain state of 370-3300 with a pass band at the 3 dB point of 70 kHz.

The output from amplifier 89 is applied via line 92 to the slicer detector circuitry which comprises a comparator that detects transitions occurring at the 1.34 volts transition point and when such transitions are detected, the slicer circuitry provides 15 volts transitions on line 96, which signal is applied to the detector 98. Before the receiver window is opened, line 122 is high, which results in a transistor 190 being switched into conduction which charges capacitors 192 and 194 to a voltage level of approximately 15 volts (i.e., the supply voltage level). When the receiving window is opened, the signal on line 122 is then low and transistor 190 is switched off, which places the detector in condition to detect the presence of a reflected chirp, which if present and detected, results in line 96 being switched low and the capacitors 192 and 194 are slowly discharged when the slicer is operating. When the level reaches approximately 5 volts, a comparator 196, which is part of the detector 98, is tripped and produces a signal which is applied on line 100. That signal is applied to gates 198 and 200 that are demultiplexed by operation of the enable signal on line 50 through the gate 202 and line 204 to the other input of a NAND gate to trigger either one of the retriggerable oneshots 104 or 106. The time constant is determined by capacitors 192 and 194 and a resistor 206 and are selected such that a single transition detected by the slicer is not sufficient to discharge capacitors 192 and 194 so that the comparator 196 is tripped, it being preferred that there be a signal having a duration of approximately 75 to 100 microseconds necessary to accomplish this operation. As previously mentioned, the cycle timer starts a transmission of sound for each of the modules every 10 milliseconds and the retriggerable one-shot 104 has its parameters selected so that it will time-out after approximately 25 milliseconds. Thus, as the chirps are reflected and detected indicating the presence of a web, the one-shot will be retriggered every 10 milliseconds and the output line 112 will be true indicating that the web is present. If two successive transmitted sound signals are not detected, then this is an indication that the web is not present and the signal level on line 112 will go low, which (see FIG. 5B) results in one of the relays 108 or 110 being activated for the purpose of shutting down the press.

The circuitry also includes a provision for providing hysteresis in the operation of the comparator 196 and to this end, the hysteresis circuit 124 is provided and includes logic gates 206, 208 and 210 in combination with line 126 that is connected to a resistor 212, which in combination with resistors 214 and 216 determine the reference voltage for the comparator 196. When the output of the OR gate for low signals 210 is low, the reference voltage is at the 5 volts level. When line 126 is high, then the reference level is increased to 10 volts. The logic is defined so that once one of the retriggerable one-shots 104 or 106 times out, the reference voltage for comparator 196 is changed to 10 volts. From the foregoing, it should be appreciated that an improved sonic web break detector has been shown and described which has many desireable attributes, including efficient and reliable operation. The compact design in terms of hardware and circuitry results in superior operation and can be produced at attractive manufacturing costs. While the detailed description has been done in the environment of a web break detector for printing presses, it should be understood that it is useful in other types of industries and applications other than printing presses as should be appreciated.

It should also be appreciated that while the preferred embodiment has been described utilizing pairs of modules for detecting breaks in the outer edges of the web, certain applications may not require pairs of modules, but in fact may have only one detector module. In such instances, the multiplexing aspects of the circuitry would not be required, and modification of the detailed circuitry for such an application is well within the capability of one skilled in the art.

While various embodiments of the present invention have been shown and described, it should be understood that various alternatives, substitutions and equivalents can be used, and the present invention should only be limited by the claims and equivalents thereof.

Various features of the present invention are set forth in the following claims.

What is claimed is:

1. Apparatus for monitoring a web of material being moved by web handling machinery having operating control means, said apparatus having two web monitoring modules for monitoring the web adjacent thereto, said apparatus comprising:

means included in each module for intermittently emitting at least one burst of high frequency sonic energy toward the web at a predetermined frequency and at a predetermined angle relative to a line generally perpendicular to the plane of the web;

means included in each module for detecting sonic energy reflected from the web, and for generating electrical signals that selectively indicate the presence and absence of reflected sonic energy;

means for controlling each of said emitting means and each of said detecting means whereby each of said emitting means is selectively triggered to emit said sonic energy for a predetermined time period and at a predetermined rate, and each of said detecting means is selectively activated for a predetermined time duration which beings after a predetermined delay relative to the time in which said emitting means has been triggered, said controlling means alternatingly triggering the emitting means of the two modules and alternatingly activating the detecting means of the two modules; and, means responsive to said electrical signal indicating the absence of said energy for generating a machinery control signal for application to the operating control means of the machinery to stop the web handling machinery.

2. Apparatus as defined in claim 1 wherein each of said emitting means produces sonic energy having a frequency of approximately 215 kiloHertz.

3. Apparatus as defined in claim 1 wherein each of said emitting means produces sonic energy for a time period of approximately 150 microseconds at a rate of 10 milliseconds.

4. Apparatus as defined in claim 1 wherein said predetermined delay comprises the time required for the sonic energy to pass from one of said emitting means to said detecting means associated therewith.

5. Apparatus as defined in claim 4 wherein said predetermined delay is approximately 200 microseconds.

6. Apparatus as defined in claim 1 wherein said predetermined time duration is approximately 1.4 milliseconds.

7. Apparatus as defined in claim 1 wherein said control signal generating means comprising a means for detecting electrical signals that are indicative of a predetermined number of successive bursts of sonic energy being detected, said machinery control signal being generated in the absence of electrical signals being received that are indicative of two successive bursts not being detected.

8. Apparatus as defined in claim 7 wherein said control signal generating means comprises a retriggerable monostable multivibrator that generates said control signal in the absence of said electrical signals being applied thereto to retrigger the same.

9. Apparatus as defined in claim 8 wherein said monostable multivibrator generates said control signal in the absence of said electrical signals being applied thereto within a time period of approximately 25 milliseconds.

10. Apparatus as defined in claim 1 wherein each of said emitting means and each of said detecting means comprise a piezoelectric transducer.

11. Apparatus as defined in claim 10 wherein each of said emitting means comprises a piezoelectric transducer adapted to produce sonic energy at a frequency of approximately 215 kHz when driven at a voltage alternating between approximately +24 volts and −24 volts.

12. Apparatus as defined in claim 10 wherein each of said detecting means comprises a piezoelectric transducer adapted to detect sonic energy and produce an electric signal responsive to the detection thereof.

13. Apparatus as defined in claim 10 wherein each of said emitting means and each of said detecting means are separate and independent piezoelectric transducers and said predetermined angle is within the range of approximately 7 degrees to approximately 15 degrees.

14. Apparatus as defined in claim 13 wherein each of said transducers have a front surface, said apparatus including a thin film adhesively applied thereto for the purpose of protecting the same and for facilitating cleaning thereof.

15. Apparatus as defined in claim 14 wherein said thin film has a thickness within the range of approximately 2 mils and approximately 4 mils.

16. Apparatus as defined in claim 15 wherein said film is adhesively applied to the front surface of said transducer with an adhesive having a thickness of approximately 1 mil.

17. Apparatus as defined in claim 14 wherein said transducers are mounted in said module adjacent one another such that the front surfaces thereof are recessed relative to the front surface of the module.

18. Apparatus as defined in claim 13 wherein front surface of said module has a depression in which said transducers are located, with the depression having a generally circular shape in plan view and a generally concave shape in cross section.

19. Apparatus as defined in claim 18 wherein said depressions intersect one another, so as to produce a generally straight line in plan view.

20. Apparatus for monitoring a web of material being moved by web handling machinery having operating control means, said apparatus having at least two web monitoring modules for monitoring the web adjacent thereto, said apparatus comprising:

cycle timer means for producing cycle timing signals having a predetermined duty cycle;

transmit timer means operatively connected to said cycle timer means and producing an electrical signal having a predetermined time duration in response to receiving cycle timing signals generated by said cycle timer means;

a pair of transmitter piezoelectric transducers, each being adapted to produce sonic energy in response to a driving signal being applied thereto;

means for producing a driving signal for operating said sonic energy transmitting piezoelectric transducers at a predetermined frequency;

multiplexing means operatively connected to each of said cycle timer means, transmit timer means and driving signal producing means for alternatingly applying said driving signal to each of said transmitter transducers for said predetermined time duration in response to said timing signals being produced by said cycle timer means and in response to said electrical signal being generated by said transmit timer means;

a pair of receiver piezoelectric transducers, each being adapted to produce electrical output signals in response to detecting sonic energy;

amplifier means operatively connected to said receiver transducers for amplifying signals received thereby, and comprising a plurality of stages of bandpass amplifiers for amplifying signals having a frequency near said predetermined frequency, and providing amplified output signals;

means connected with said transmit timer means for producing an electrical receiver window signal having a predetermined duration and a start time coincident with the electrical signal produced by said transmit timer means;

means operatively connected to said amplifier means for determining the presence or absence of receiver transducer output signals near said predetermined frequency and for generating a web break indicating signal in response to the absence of such output signals.

21. Apparatus as defined in claim 20 including variable gain control means connected to said receiver delay means and said amplifier means for varying the gain produced by at least one stage of bandpass amplifier, said gain being no greater than approximately one when said variable gain control means is actuated and substantially greater than one immediately before the end of the receiver window time duration.

22. Apparatus as defined in claim 20 wherein said driving means drives said transmitter piezoelectric transducers at a frequency of approximately 215 kHz at a voltage alternating between approximately +24 volts and −24 volts.

23. Apparatus as defined in claim 22 wherein said driving means comprises a bi-polar push-pull driver that have a tristating capability and is operable to drive the transmitter transducers by alternately applying +24 volts and −24, volts thereto.

24. Apparatus as defined in claim 22 wherein said amplifier means includes at least one stage of band pass amplifier that is adapted to produce a variable gain from approximately one to approximately 13 in response to a variable gain control signal being applied thereto.

25. Apparatus as defined in claim 21 wherein said window signal producing means comprises a means operatively connected to said transmit timer means for producing a predetermined delay in response to receiving said electrical signal from said transmit timer means and a means for producing a receiver window electrical signal, said last means being operatively connected to said delay producing means and having an output connected to said variable gain control producing means.

26. Apparatus as defined in claim 25 wherein said predetermined delay comprises the time required for the sonic energy to pass from said emitting means to said detecting means.

27. Apparatus as defined in claim 25 wherein said predetermined delay is approximately 200 microseconds.

28. Apparatus as defined in claim 20 wherein said predetermined time duration for the electrical signal produced by said transmit timer means is approximately 1.4 milliseconds.

29. Apparatus as defined in claim 20 wherein said output signal determining means comprising a means for detecting electrical signals that are indicative of a predetermined number of successive bursts of sonic energy being detected, said web break indicating signal being generated in the absence of electrical signals being received that are indicative of two successive bursts not being detected.

30. Apparatus as defined in claim 29 wherein said output signal determining means comprises a retriggerable monostable multivibrator that generates said web break indicating signal in the absence of said receiver transducer output signals being applied thereto to retrigger the same.

31. Apparatus as defined in claim 30 wherein said monostable multivibrator generates said web break indicating signal in the absence of said receiver transducer output signals being applied thereto within a time period of approximately 25 milliseconds.

32. Apparatus for monitoring a web of material being moved by web handling machinery having operating control means, said apparatus having at least two web monitoring modules for monitoring the web adjacent thereto, said apparatus comprising:

cycle timer means for producing cycle timing signals having a predetermined duty cycle;

transmit timer means operatively connected to said cycle timer means and producing an electrical signal having a predetermined time duration in response to receiving cycle timing signals generated by said cycle timer means;

a pair of transmitter piezoelectric transducers, each being adapted to produce sonic energy in response to a driving signal being applied thereto;

means for producing a driving signal for operating said sonic energy transmitting piezoelectric transducers at a predetermined frequency;

multiplexing means operatively connected to each of said cycle timer means, transmit timer means and driving signal producing means for alternatingly applying said driving signal to each of said transmitter transducers for said predetermined time duration in responsive to said timing signals being produced by said cycle timer means and in response to said electrical signal being generated by said transmit timer means;

a pair of receive piezoelectric transducers, each being adapted to produce electrical output signals in response to detecting sonic energy;

amplifier means operatively connected to said receiver transducers for amplifying signals received thereby, said amplifier means amplifying signals having a frequency near said predetermined frequency, and providing amplified output signals;

means connected with sad transmit timer means for producing an electrical receiver window signal having a predetermined duration and a start time coincident with the electrical signal produced by said transmit timer means;

means operatively connected to said amplifier means for determining the presence or absence of receiver transducer output signals near said predetermine frequency and for generating a web break indicating signal in response to the absence of such output signals.

33. Apparatus for monitoring a web of material being moved by web handling machinery having operating control means, said apparatus having at least one web monitoring module for monitoring the web adjacent thereto, said apparatus comprising:

means for intermittently emitting at least one burst of high frequency sonic energy toward the web at a predetermined frequency and at a predetermine angle relative to a line generally perpendicular to the plane of the web;

means for detecting sonic energy reflected from the web, and for generating electrical signals that selectively indicate the presence and absence of reflected sonic energy;

each of said emitting means and said detecting means comprising separate and independent piezoelectric transducers, each of said transducers having a front surface and a thin film adhesively applied thereto for the purpose of protecting the same and for facilitating cleaning thereof;

means for controlling said emitting means and said detecting means whereby said emitting means is triggered to emit said sonic energy for a predetermined time period and at a predetermined rate, and said detecting means is activated for a predetermined time duration which begins after a predetermined delay relative to the time in which said emitting means has been triggered; and, means responsive to said electrical signals indicating the absence of said energy for generating a machinery control signal for application to the operating control means of the machinery to stop the web handling machinery.

34. Apparatus as defined in claim 33 including two web monitoring modules and said controlling means alternatingly triggers the emitting means of the two modules and alternatingly activates the detecting means of the two modules.

* * * * *

UNITED STATES PATENT AND TRADEMARK OFFICE
CERTIFICATE OF CORRECTION

PATENT NO. : 5,036,706

DATED : August 6, 1991

INVENTOR(S) : Gnuechtel et al.

It is certified that error appears in the above-identified patent and that said Letters Patent is hereby corrected as shown below:

Column 1, line 29, change "utilizes" to --utilized--.

Column 3, line 14, change "presses" to --press--.

Column 4, line 52, change "5" to --5°--; change "10" to --10°--; change "7" to --7°--.

Column 11, line 31, change "signal" to --signals--.

Column 12, line 36, after "wherein" insert --the--.

Column 13, line 40, after "-24" delete ",".

Column 14, line 41, change "responsive" to --response--.

Column 14, line 46, change "receive" to --receiver--.

Column 14, line 53, change "sad" to --said--.

Column 14, line 60, change "predetermine" to --determined--.

Signed and Sealed this

Third Day of November, 1992

*Attest:*

DOUGLAS B. COMER

*Attesting Officer*   *Acting Commissioner of Patents and Trademarks*